(12) United States Patent
Shimuta et al.

(10) Patent No.: US 11,647,921 B2
(45) Date of Patent: May 16, 2023

(54) BREATHING SENSING DEVICE

(71) Applicant: Murata Manufacturing Co., Ltd., Nagaokakyo (JP)

(72) Inventors: Toru Shimuta, Nagaokakyo (JP); Takenobu Maeda, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 344 days.

(21) Appl. No.: 16/398,540

(22) Filed: Apr. 30, 2019

(65) Prior Publication Data

US 2019/0254571 A1 Aug. 22, 2019

Related U.S. Application Data

(63) Continuation of application No. PCT/JP2017/040798, filed on Nov. 13, 2017.

(30) Foreign Application Priority Data

Nov. 15, 2016 (JP) .............................. JP2016-222388

(51) Int. Cl.
*A61B 5/113* (2006.01)
*A61B 5/08* (2006.01)
*A61B 5/00* (2006.01)

(52) U.S. Cl.
CPC ............... *A61B 5/113* (2013.01); *A61B 5/08* (2013.01); *A61B 5/0816* (2013.01); *A61B 5/6823* (2013.01); *A61B 5/6832* (2013.01)

(58) Field of Classification Search
CPC ............... A61B 5/6823; A61B 5/6832; A61B 2562/0261; A61B 5/1116; A61B 5/1117;

(Continued)

(56) References Cited

U.S. PATENT DOCUMENTS 3,517,999 A * 6/1970 Weaver ................ A61B 5/1135
600/595
4,930,518 A * 6/1990 Hrushesky ........... A61B 5/0205
600/484

(Continued)

FOREIGN PATENT DOCUMENTS

EP 2438854 A2 * 4/2012 ......... A61B 5/02438
GB 2138144 A * 10/1984 ............. A61B 5/113

(Continued)

OTHER PUBLICATIONS

Víctor Manuel Castro, Nestor Andrés Muñoz, Antonio José Salazar, "A stethoscope with wavelet separation of cardiac and respiratory sounds for real time telemedicine implemented on field-programmable gate array," Jan. 28, 2015, Proc. SPIE 9287, 10th International Symposium on Medical Information Processing and Analysis, 92870L (Year: 2015).*

(Continued)

*Primary Examiner* — Daniel L Cerioni
*Assistant Examiner* — Jonathan E. Cooper
(74) *Attorney, Agent, or Firm* — ArentFox Schiff LLP

(57) ABSTRACT

A breathing sensing device that detects breathing of a subject, the breathing sensing device including a film-shaped sensor configured to adhere to a body surface of the subject from a region corresponding to a xiphoid process of a sternum of the subject to a region corresponding to an epigastrium of the subject. The sensor is configured to detect the breathing of the subject by detecting relative positional changes between the region corresponding to the xiphoid process and the region corresponding to the epigastrium.

19 Claims, 10 Drawing Sheets

(58) Field of Classification Search
CPC ... A61B 5/1118; A61B 5/1135; A61B 5/0205; A61B 5/02438; A61B 5/0823; A61B 5/0826; A61B 5/087; A61B 5/7221; A61B 2562/0219; A61B 7/003; A61B 5/113
USPC .................................................. 600/536, 534
See application file for complete search history.

(56) References Cited

U.S. PATENT DOCUMENTS

| | | | | |
|---|---|---|---|---|
| 5,448,996 | A * | 9/1995 | Bellin | A61B 5/0205 600/595 |
| 5,749,365 | A | 5/1998 | Magill | |
| 6,064,910 | A * | 5/2000 | Andersson | A61B 7/003 600/528 |
| 6,383,143 | B1 * | 5/2002 | Rost | A61B 5/6833 600/534 |
| 2003/0163287 | A1 * | 8/2003 | Vock | A61B 5/1118 702/187 |
| 2004/0147851 | A1 | 7/2004 | Bignall | |
| 2005/0039699 | A1 | 2/2005 | Sato | |
| 2005/0119586 | A1 * | 6/2005 | Coyle | A61B 5/4818 600/538 |
| 2008/0275356 | A1 | 11/2008 | Stasz | |
| 2009/0015108 | A1 * | 1/2009 | Ishimasa | A61B 5/7278 600/324 |
| 2010/0069772 | A1 * | 3/2010 | Henke | A61B 5/4806 600/534 |
| 2010/0198084 | A1 | 8/2010 | Kim | |
| 2014/0275887 | A1 * | 9/2014 | Batchelder | A61B 5/335 600/301 |
| 2015/0087923 | A1 * | 3/2015 | Bardy | A61B 5/1032 |
| 2015/0257654 | A1 | 9/2015 | Bennett-Guerrero | |
| 2016/0324462 | A1 * | 11/2016 | Hämäläinen | A61B 5/02055 |
| 2018/0042486 | A1 * | 2/2018 | Yoshizawa | A61B 5/335 600/301 |
| 2019/0167186 | A1 * | 6/2019 | Mlynczak | A61B 5/7282 |

FOREIGN PATENT DOCUMENTS

| | | | | |
|---|---|---|---|---|
| JP | H07500748 | A | | 1/1995 |
| JP | 2000350716 | A | | 12/2000 |
| JP | 2001269322 | A | | 10/2001 |
| JP | 2004536654 | A | | 12/2004 |
| JP | 2010525872 | A | | 7/2010 |
| JP | 2011501678 | A | | 1/2011 |
| JP | 2012065729 | A | | 4/2012 |
| JP | 2013066570 | A | | 4/2013 |
| JP | 2013198618 | A | | 10/2013 |
| JP | 2016190022 | A * | 11/2016 | ........... A61B 5/7278 |
| WO | WO-0197691 | A1 * | 12/2001 | ............ A61B 7/003 |
| WO | 03067967 | A1 | 8/2003 | |
| WO | WO-2014128090 | A1 * | 8/2014 | ........... A61B 5/7282 |
| WO | WO-2016027613 | A1 * | 2/2016 | ............ B32B 27/36 |

OTHER PUBLICATIONS

International Search Report issued for PCT/JP2017/040798, dated Dec. 26, 2017.
Written Opinion of the International Searching Authority issued for PCT/JP2017/040798, dated Dec. 26, 2017.

* cited by examiner

BREATHING SENSING DEVICE

CROSS-REFERENCE TO RELATED APPLICATIONS

The present application is a continuation of PCT/JP2017/040798 filed Nov. 13, 2017 which claims priority to Japanese Patent Application No. 2016-222388, filed Nov. 15, 2016, the entire contents of each of which are incorporated herein by reference.

TECHNICAL FIELD

The present disclosure relates to a breathing sensing device that detects breathing of a subject.

BACKGROUND

Generally, as examples of breathing sensing devices, a device in which a belt incorporating a piezoelectric film is worn and a device that detects changes in the curvature of the chest or abdomen of a subject are known (for example, refer to Patent Documents 1 and 2): Patent Document 1: Japanese Unexamined Patent Application Publication (Translation of PCT Application) No. 2010-525872 and Patent Document 2: Japanese Unexamined Patent Application Publication (Translation of PCT Application) No. 2004-536654.

In the case of the breathing sensing device disclosed in Patent Document 1, a belt incorporating a piezoelectric film is worn around the chest or abdomen of the subject and the breathing of the subject is detected in accordance with a tensile force acting on the belt. However, in the case of such a configuration in which a belt is worn by the subject, there is a risk that the subject will feel significant discomfort and that the subject's breathing will be affected such that the subject will find it more difficult to breath while wearing the belt.

In addition, in the case of the breathing sensing device disclosed in Patent Document 2, a sensor is attached to the chest or abdomen of the subject and the breathing of the subject is detected by detecting changes in the curvature of the chest or abdomen of the subject. However, there is a problem with this configuration in that the sensitivity with which abdominal breathing is detected is poor when the sensor is attached to the chest of the subject and the sensitivity with which chest breathing is detected is poor when the sensor is attached to the abdomen of the subject. Furthermore, there is also a problem in that the breathing sensing device is large in order to detect changes in curvature.

SUMMARY

The present disclosure was made in light of the above-described problems, and it is an object thereof to provide a breathing sensing device that can accurately detect both chest breathing and abdominal breathing of a subject.

In order to solve the above-described problem, the present disclosure provides a breathing sensing device that detects the breathing of a subject. The breathing sensing device includes a film-shaped sensor that is configured to adhere to a body surface of the subject from a region corresponding to a xiphoid process of a sternum of the subject to a region corresponding to an epigastrium of the subject. The sensor is configured to detect the breathing of the subject by detecting relative positional changes between the region corresponding to the xiphoid process and the region corresponding to the epigastrium.

According to the present disclosure, the film-shaped sensor is adhered to the body surface of the subject from the region corresponding to the xiphoid process to the region corresponding to the epigastrium. Consequently, the sensor deforms when the body surface of the subject moves due to breathing and relative changes between the region corresponding to the xiphoid process and the region corresponding to the epigastrium can be detected. At this time, a relative displacement is generated between the region corresponding to the xiphoid process and the region corresponding to the epigastrium in both chest breathing and abdominal breathing. Therefore, the sensor can detect both chest breathing and abdominal breathing.

Furthermore, since the film-shaped sensor is only configured to adhere from the region corresponding to the xiphoid process to the region corresponding to the epigastrium, the breathing sensing device can be reduced in size compared with a device in which a belt or the like is worn by the subject.

In addition, breathing can be detected without the subject being compressed by a belt or the like, and therefore a situation in which the breathing of the subject is affected by the device can be suppressed. Thus, a feeling of discomfort experienced by the subject is reduced and the degree of non-invasiveness can be increased.

In the present disclosure, the sensor consists of a piezoelectric film sensor and detects the breathing of the subject by detecting a signal generated by deformation of the piezoelectric film sensor.

According to the present disclosure, the sensor consists of a piezoelectric film sensor. Consequently, the displacement speed of a relative change between the region corresponding to the xiphoid process of the subject and the region corresponding to the epigastrium of the subject can be measured, and therefore minute body movements of the subject caused by breathing can be accurately detected. In addition, the breathing of the subject can be detected without being affected by external disturbances such as perspiration.

In the present disclosure, the sensor has a rectangular shape, has a high degree of sensitivity to extension in a length direction extending from a chest of the subject to an abdomen of the subject or bending in a front-back direction perpendicular to the length direction and has a low degree of sensitivity to twisting.

According to the present disclosure, the sensor has a rectangular shape, has a high degree of sensitivity to extension in the length direction extending from the chest of the subject to the abdomen of the subject or bending in the front-back direction perpendicular to the length direction and has a low degree of sensitivity to twisting. As a result, in the case where the subject changes his/her posture and twisting or the like occurs in the trunk of his/her body, erroneous detection of something other than breathing caused by deformation in the direction in which the sensor has low sensitivity can be suppressed and the sensor can detect variations due to breathing with high accuracy.

The present disclosure further includes a signal processing unit that is configured to distinguish output from the sensor caused by breathing, a sound signal, and a deformation signal caused by beating of a heart based on frequency signals of the output having different frequency components from each other.

According to the present disclosure, the signal processing unit may use a frequency filter or the like to distinguish the frequency components. As a result, specific signals can be detected by changing the frequency band that is to be detected, and therefore a plurality of signals can be accurately detected using simple processing without the occurrence of erroneous recognition.

In addition, since the deformation signal caused by breathing and the sound signal are distinguished/separated and detected, abnormal breathing can be accurately detected by comparing these two signals. Furthermore, the heartbeat interval (heart rate) can be calculated using the deformation signal caused by beating of the heart, and therefore a heart abnormality can be detected from the heart rate.

The present disclosure further includes a signal processing unit that separates a signal caused by breathing and a signal caused by beating of the heart as period signals having different periods from each other.

According to the present disclosure, the signal caused by breathing and the signal caused by beating of the heart are separated as period signals having different periods from each other using a pattern matching method, an autocorrelation technique, or the like. Thus, even in the case where frequency components of the individual signals overlap and cannot be separated from each other using a frequency filter, specific signals can be detected by changing the period to be detected. Therefore, a plurality of signals can be accurately detected without the occurrence of erroneous recognition.

In addition, the breathing rate of the subject can be accurately detected by estimating breathing fluctuations from the signal caused by beating of the heart and comparing the breathing fluctuations and the signal caused by breathing.

The present disclosure further includes a battery that supplies a power supply voltage to the signal processing unit, the signal processing unit converting a signal output from the sensor into a digital signal and outputting the digital signal to an external device.

The present disclosure further includes a battery that supplies a power supply voltage to the signal processing unit, the signal processing unit converting a signal output from the sensor into a digital signal and outputting the digital signal to an external device. As a result, data regarding breathing can be output to an external device in a cable-free manner, and therefore a non-invasive breathing sensing device can be provided that does not constrict the subject and does not cause the subject to feel stressed or tense. Furthermore, since the device is non-invasive, measurements can also be taken over a long period of time and during everyday activities.

The present disclosure further includes an acceleration sensor that detects a posture and an activity amount of the subject from an acceleration signal.

The present disclosure further includes an acceleration sensor that detects a posture and an activity amount of the subject from an acceleration signal. Thus, information regarding the posture and activity amount of the subject, which are factors that affect breathing and the beating of the heart can be simultaneously obtained, and therefore an abnormality in the breathing or the beating of the heart can be accurately detected. For example, breathing slowly becomes deeper during deep sleep and beating of the heart also becomes slower. In contrast, breathing and beating of the heart both become faster while walking or during exercise. Therefore, the accuracy with which an abnormality is detected can be improved by simultaneously obtaining information regarding posture and activity amount.

DETAILED DESCRIPTION

Figure 1:
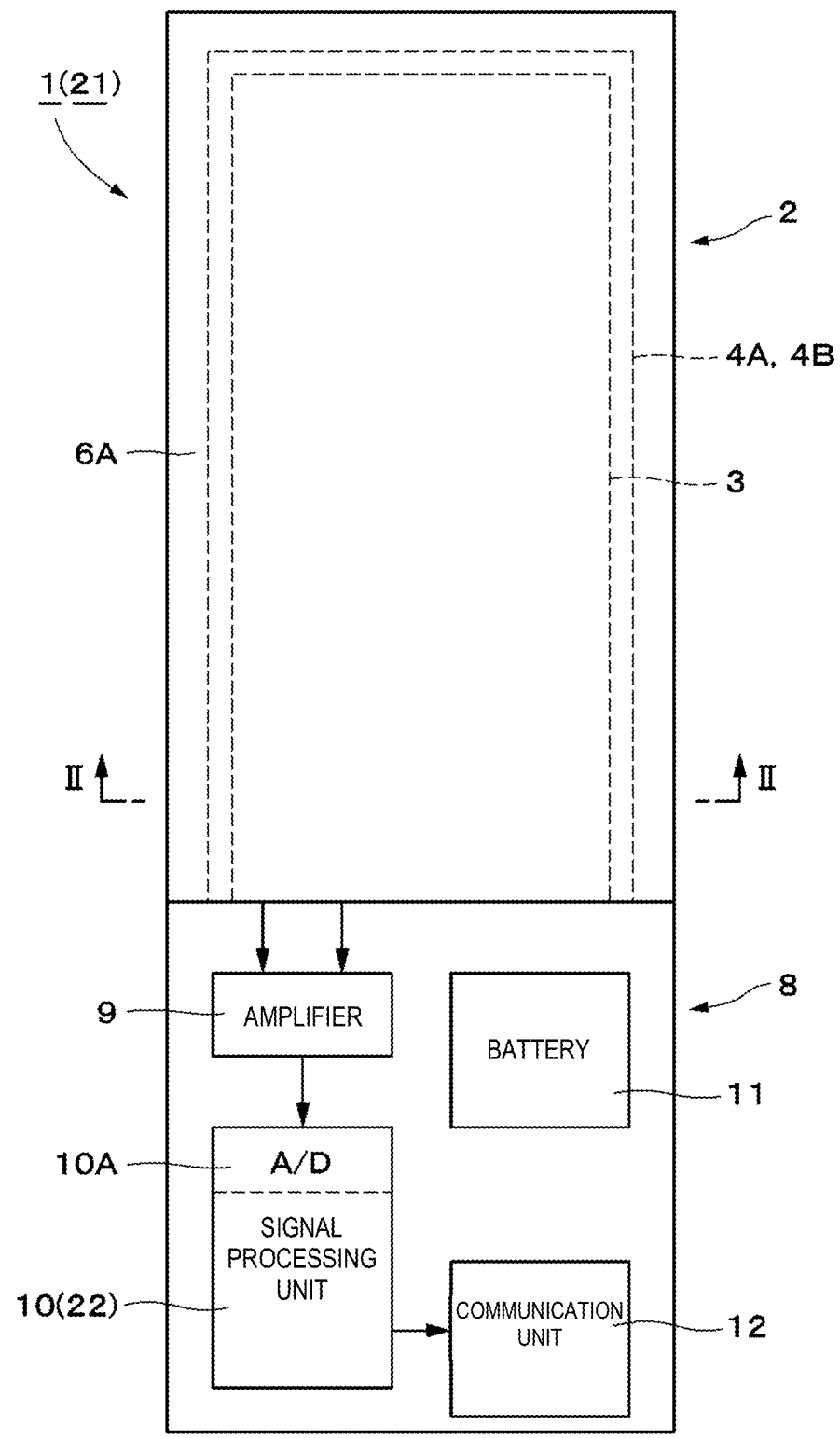
FIG. 1 is a front view illustrating a breathing sensing device according to a first embodiment of the present disclosure.
Figure 2:
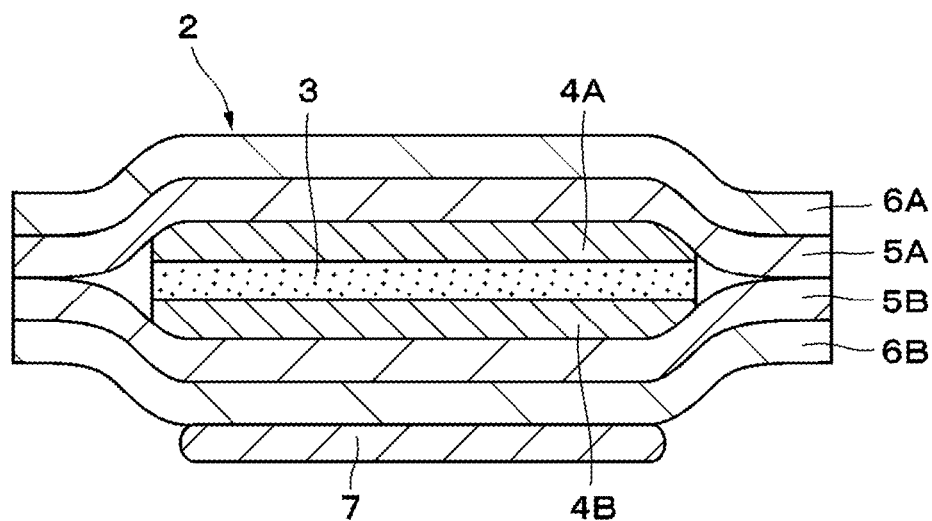
FIG. 2 is a sectional view seen in the direction of arrows II-II in FIG. 1.

Hereafter, breathing sensing devices and embodiments of use will be described in detail while referring to the drawings.

A first embodiment will be described while referring to FIGS. 1 to 11. In exemplary aspects, a breathing sensing device 1 according to the first embodiment includes a sensor member 2 that detects the breathing of a subject "Obj" (not shown) and a body part 8 that is configured to perform signal processing on the detected breathing.

Figure 3:
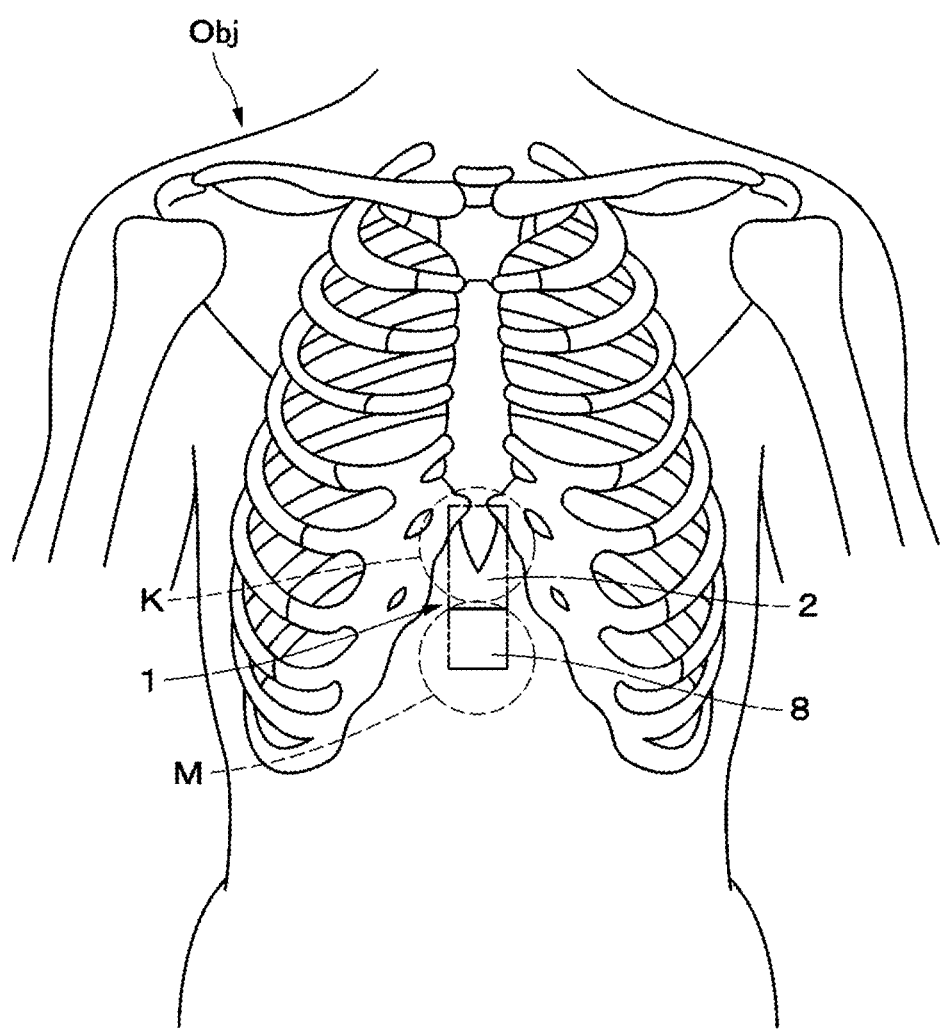
FIG. 3 is an explanatory diagram illustrating a case in which the breathing sensing device is adhered from a region corresponding to the xiphoid process of a subject to a region corresponding to the epigastrium of the subject.

The sensor member 2 has a rectangular shape overall, in some aspects, and is provided so as positioned at one end (upper end in FIG. 1) of the breathing sensing device 1. The sensor member 2 includes a film sensor 3 (e.g., piezoelectric film sensor or the like), first and second electrodes 4A and 4B, insulating sheets 5A and 5B, shields 6A and 6B, and so forth. As illustrated in FIG. 3, the sensor member 2 is adhered to a body surface of the subject Obj using an adhesive member 7, which is described later, from a region K corresponding to the xiphoid process of the sternum of a subject to a region M corresponding to the epigastrium of the subject.

Specifically, a length direction dimension (up-down direction dimension) of the sensor member 2 is set to be a dimension of around 4-10 cm for example, and a width direction dimension of the sensor member 2 is set to be a dimension of around 0.5-4 cm, for example. In addition, a thickness direction dimension of the sensor member 2 is set to be a dimension of around 0.1-1 mm, for example. Thus, the length direction of the sensor member 2 extends from a lower end of the chest of the subject Obj to an upper end of the abdomen of the subject Obj. As a result, the sensor member 2 is deformed by movement of the body surface of the subject Obj caused by breathing, and the breathing of the subject Obj can be detected by detecting relative changes between the region K corresponding to the xiphoid process and the region M corresponding to the epigastrium.

The piezoelectric film sensor 3 is provided so as to be located inside the sensor member 2. The piezoelectric film sensor 3 is composed of a thin film (thin plate) that functions as a film-shaped sensor and is caused to generate an electrical signal as a result of the film being deformed. Here, for example, the piezoelectric film sensor 3 may be a piezoelectric polymer film sensor composed of polyvinylidene fluoride (PVDF), polylactic acid or the like or a film sensor obtained by forming an inorganic thin film composed of aluminum nitride (AlN), lead zirconate titanate (PZT), or the like on a substrate such as a resin film.

In this case, polylactic acid exhibits shear piezoelectric characteristics, and therefore when the film is cut into a strip shape at an angle of 45° with respect to the alignment direction of the molecules, the sensitivity of the film to bending and extension can be made high and the sensitivity of the film to twisting can be made low. Therefore, it is preferable that polylactic acid be used for the piezoelectric film sensor 3 in order to make the accuracy with which breathing of the subject Obj is detected high and to make the sensitivity with which twisting caused by changes in the posture of the subject Obj low. Thus, by forming the piezoelectric film sensor 3 using polylactic acid, sensitivity to stretching of the subject Obj in the length direction and sensitivity to bending in a front-back direction (front-back direction of subject Obj, i.e., thickness direction of sensor member 2) that is perpendicular to the length direction are made high, and sensitivity to twisting of the subject Obj is made low.

The first and second electrodes 4A and 4B are located inside the sensor member 2 and are respectively provided on both sides of the piezoelectric film sensor 3 in the thickness direction of the piezoelectric film sensor 3. The first and second electrodes 4A and 4B are formed using a conductive thin film composed of a conductive material such as a metal material, indium tin oxide (ITO) or the like, or carbon or the like. The first and second electrodes 4A and 4B detect an analog signal Sa corresponding to deformation of the piezoelectric film sensor 3 and output the detected analog signal Sa to an amplifier 9 of the body part 8. In this case, since a very small deformation is to be detected, the first and second electrodes 4A and 4B are preferably flexible and thin.

The insulating sheets 5A and 5B are respectively provided on both sides of the piezoelectric film sensor 3 and the first and second electrodes 4A and 4B in the thickness direction. In other words, the insulating sheets 5A and 5B cover the first and second electrodes 4A and 4B from both sides in the thickness direction. The insulating sheets 5A and 5B are formed so as to have elastically deformable sheet-like shapes using an insulating soft resin material, for example. The insulating sheets 5A and 5B cover the entire surfaces of the first and second electrodes 4A and 4B and insulate the first and second electrodes 4A and 4B and the shields 6A and 6B from each other.

The shields 6A and 6B are located on the outside (outer shell) of the sensor member 2 and are respectively provided on both sides of the piezoelectric film sensor 3, the first and second electrodes 4A and 4B, and the insulating sheets 5A and 5B in the thickness direction. In other words, the shields 6A and 6B respectively cover the insulating sheets 5A and 5B from both sides in the thickness direction. The shields 6A and 6B are formed in elastically deformable sheet-like shapes using a resin film on which a conductive thin film composed of a metal foil such as silver or copper or a metal has been formed, a conductive polymer film, a conductive non-woven fabric using conductive threads, or a resin film obtained by mixing conductive particles such as carbon particles with a binder such as a resin material, for example. The shields 6A and 6B are members for shielding the piezoelectric film sensor 3 from external signals, e.g., electromagnetic waves and so forth. The shields 6A and 6B may be connected to an external ground or the like.

The adhesive member 7 is provided so as to be positioned on one side of the breathing sensing device 1 in the thickness direction. The adhesive member 7 is formed in a rectangular shape using biocompatible double-sided tape, for example. The adhesive member 7 is a member for adhering the breathing sensing device 1 from the region K corresponding to the xiphoid process of the subject Obj to the region M corresponding to the epigastrium.

The body part 8 is provided so as to be located at the other end of the breathing sensing device 1 (lower end in FIG. 1). The body part 8 includes the amplifier 9, a signal processing unit 10, a battery 11, a communication unit 12, and so forth. In this case, the body part 8 is removably connected to the sensor member 2 using a connector (not illustrated) or the like and is adhered below the sensor member 2, which is adhered to the subject Obj (refer to FIG. 3). Thus, in the case where just the sensor member 2 is damaged or dirty, just the sensor member 2 can be removed from the body part 8 and replaced.

The amplifier 9 is formed of an amplification circuit including an operational amplifier (op-amp) or the like, for example. The inputs of the amplifier 9 are respectively connected to the first and second electrodes 4A and 4B and the output of the amplifier 9 is connected to the signal processing unit 10. The amplifier 9 amplifies the analog signal Sa generated in accordance with the deformation of the piezoelectric film sensor 3 detected by the first and second electrodes 4A and 4B and outputs the amplified signal to the signal processing unit 10.

The signal processing unit 10 is provided in the body part 8 and is driven using electrical power supplied from the battery 11. An input of the signal processing unit 10 is connected to the amplifier 9. An output of the signal processing unit 10 is connected to the communication unit 12. The signal processing unit 10 is constituted by a microcomputer (CPU) and includes an analog-digital converter (A/D converter) 10A, for example. The signal processing unit 10 is a signal processing unit that detects the breathing of the subject Obj by processing the analog signal Sa detected by the piezoelectric film sensor 3 and separating the analog signal Sa into a signal Sk caused by breathing (deformation signal Skh caused by breathing and sound signal Sko caused by breathing) and a signal Ss caused by beating of the heart (deformation signal Ssh caused by beating of the heart and sound signal Sso caused by beating of the heart).

In this case, "the deformation signal Skh caused by breathing" refers to a signal generated when the body (body surface) of the subject Obj changes shape due to breathing and "the deformation signal Ssh caused by beating of the heart" refers to a signal generated when the body (body surface) of the subject Obj changes shape due to beating of the heart. In addition, "the sound signal Sko caused by breathing" refers to a signal corresponding to a breathing sound and "the sound signal Sso caused by beating of the heart" refers to a signal corresponding to a heartbeat sound. The sound signal Sko caused by breathing and the sound signal Sso caused by beating of the heart are included in a sound signal So.

The A/D converter 10A converts the analog signal Sa input from the sensor member 2 via the amplifier 9 into a digital signal Sd. At this time, the A/D converter 10A performs analog-digital conversion using a sampling period that is sufficiently shorter than the signal period of the detected analog signal Sa.

Here, after converting the analog signal Sa detected by the piezoelectric film sensor 3 into the digital signal Sd, the signal processing unit 10 performs filtering and detects the signal Sk caused by breathing (deformation signal Skh caused by breathing and sound signal Sko caused by breathing) and the signal Ss caused by beating of the heart (deformation signal Ssh caused by beating of the heart and sound signal Sso caused by beating of the heart). In this case, since the signal Sk caused by breathing and the signal Ss caused by beating of the heart have different frequencies, the signal processing unit 10 is able to separate the signal Sk caused by breathing and the signal Ss caused by beating of the heart as frequency signals having different frequency components by using a frequency filter, wavelet conversion, and so on, for example.

Furthermore, the signal processing unit 10 subjects the separated signal Sk caused by breathing and the separated signal Ss caused by beating of the heart to signal processing using a pattern matching method, an autocorrelation technique, or the like, obtains the peak interval of a correlation coefficient, and calculates a breathing interval and a heartbeat interval.

The battery 11 is provided in the body part 8 and is connected to the amplifier 9, the signal processing unit 10, the communication unit 12, and so forth. The battery 11 forms a power supply voltage circuit that supplies a power supply voltage (power) to the amplifier 9, the signal processing unit 10, the communication unit 12, and so forth. In addition, in this case, a configuration may be adopted in which a harvest antenna that receives radio waves from the outside and charges the battery 11 is provided in the body part 8.

The communication unit 12 is provided in the body part 8 and is connected to the signal processing unit 10. The communication unit 12 includes a modulation circuit that modulates a signal in accordance with any of various wireless communication standards, a transmission unit that transmits a modulated signal, and so forth. The communication unit 12 outputs the breathing and beating of the heart of the subject Obj detected by the signal processing unit 10 to a PC, a mobile terminal, a storage device, a server, or the like (none of which are illustrated).

Next, operation of the breathing sensing device 1 having the above-described configuration will be described. First, a case in which it is assumed that the subject Obj breathes by performing chest breathing and a case in which it is assumed that the subject Obj breathes by performing abdominal breathing will be described.

Figure 4:
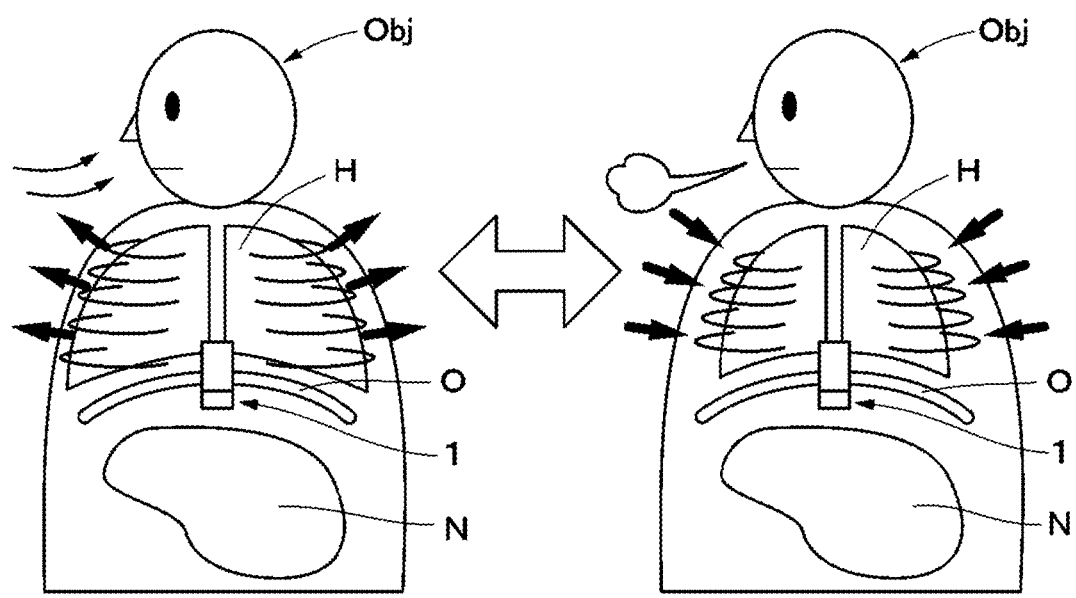
FIG. 4 is an explanatory diagram illustrating changes in body movement that occur when the subject performs chest breathing.

As illustrated in FIG. 4, when the subject Obj breathes in by performing chest breathing, the intercostal muscles, which are the muscles between the rib bones, expand in lateral directions (horizontal directions with respect to subject Obj) and the subject Obj thereby sucks air into the inside of the lungs H.

On the other hand, when the subject Obj breathes out by performing chest breathing, the intercostal muscles, which are the muscles between the rib bones, contract, the lungs H contract in the lateral directions, and the subject Obj thereby expels the air to outside the body.

Figure 5:
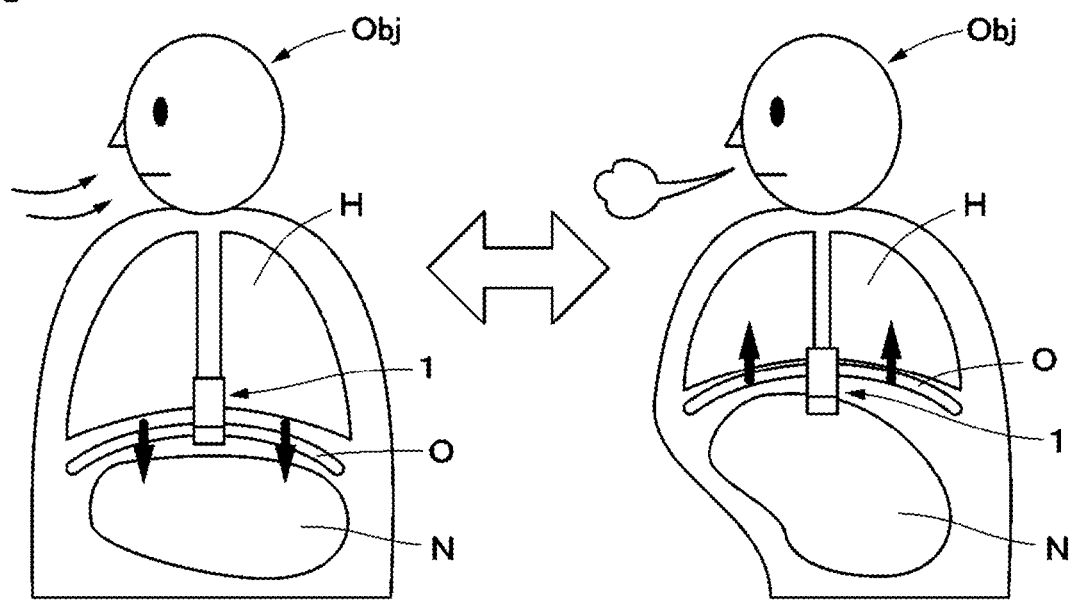
FIG. 5 is an explanatory diagram illustrating changes in body movement that occur when the subject performs abdominal breathing.

In addition, as illustrated in FIG. 5, when the subject Obj breathes in by performing abdominal breathing, a diaphragm O moves downward pressing internal organs N downward and the lungs H expand (stretch) in a vertical direction, and the subject Obj thereby sucks air into the inside of the lungs H.

On the other hand, when the subject Obj breathes out by performing abdominal breathing, the diaphragm O rises, the internal organs N are pushed upward, and the lungs contract (shrink) in the vertical direction, and the subject Obj thereby expels the air to outside the body.

In the four cases described above, the chest or abdomen changes shape and a relative change is generated between the region K corresponding to the xiphoid process and the region M corresponding to the epigastrium, and as a result the analog signal Sa is output in accordance with the speed of the deformation generated through stretching and bending of the piezoelectric film sensor 3.

Figure 6:
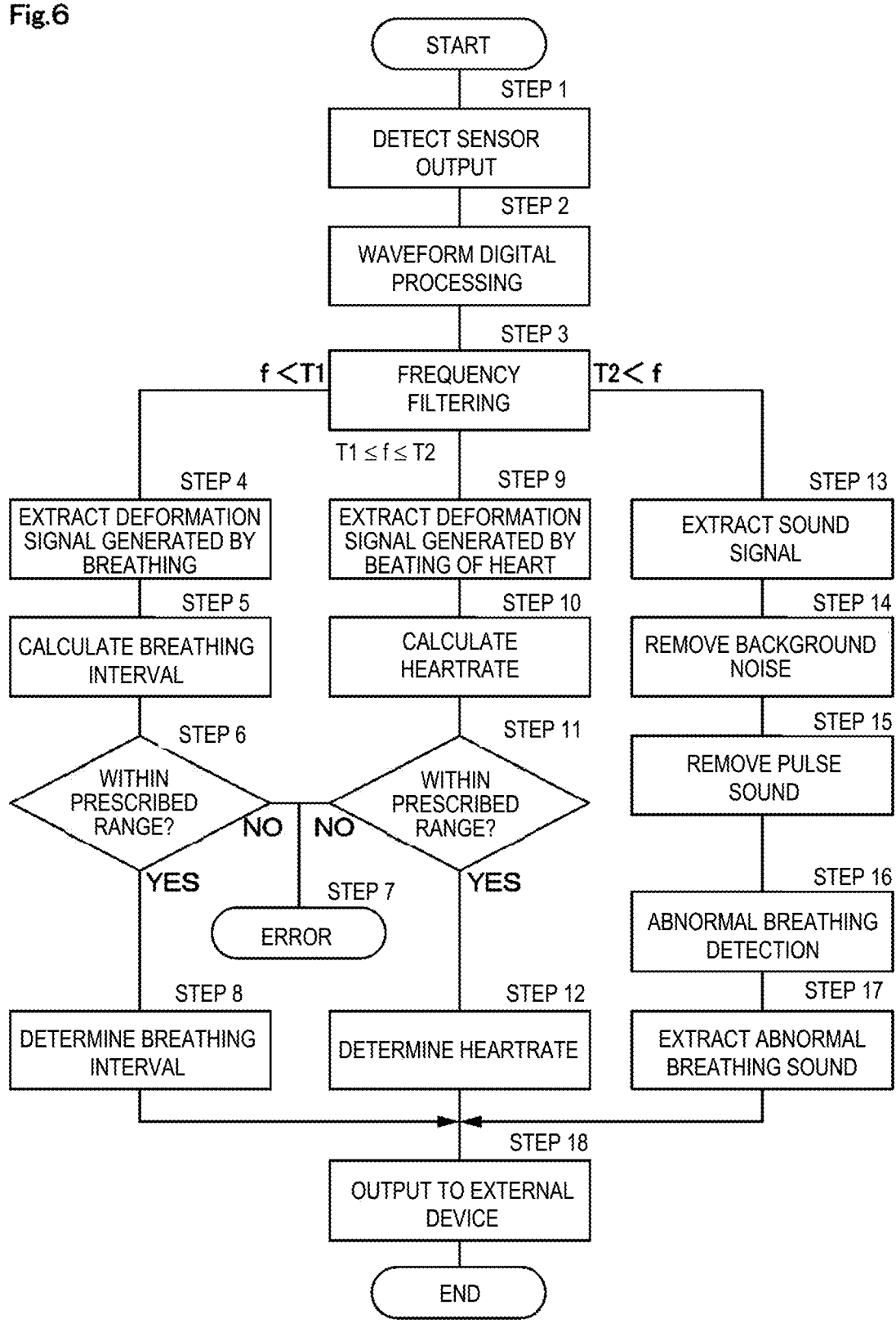
FIG. 6 is a flowchart illustrating breathing sensing processing performed by the breathing sensing device of the first embodiment.
Figure 7:
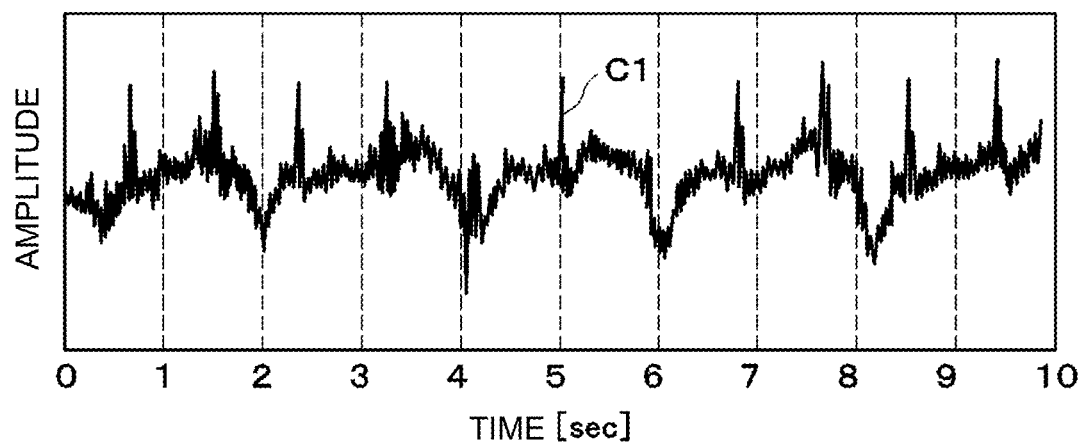
FIG. 7 is a characteristic diagram illustrating changes that occur with respect to time in an analog signal output from a piezoelectric film sensor.
Figure 8:
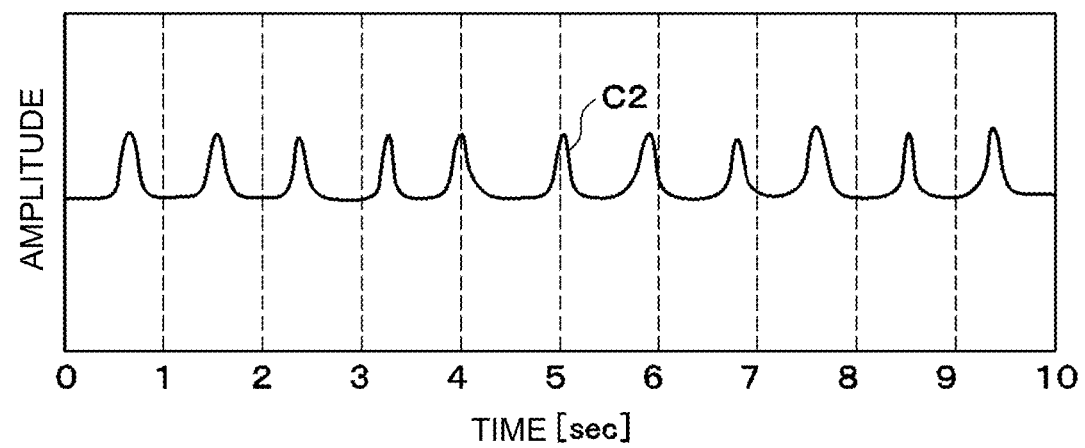
FIG. 8 is a characteristic diagram illustrating changes that occur with respect to time in a deformation signal caused by beating of the heart.
Figure 9:
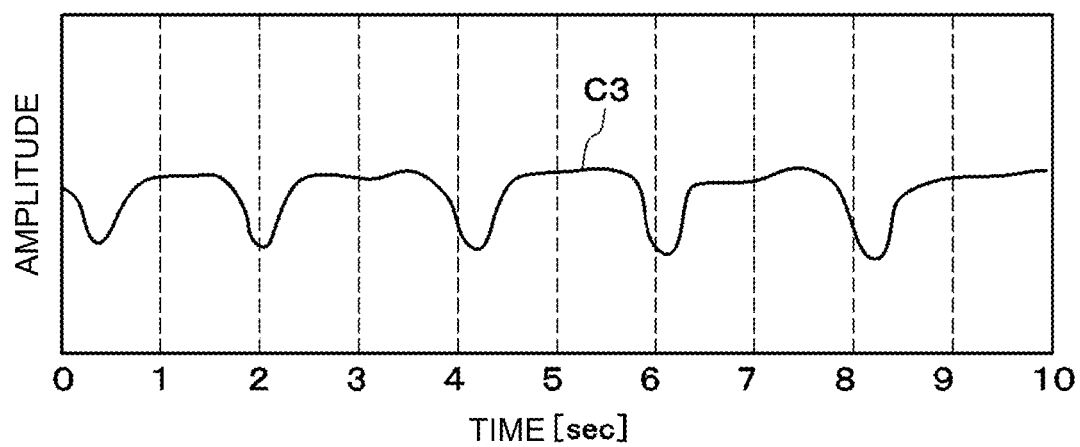
FIG. 9 is a characteristic diagram illustrating changes that occur with respect to time in a deformation signal caused by breathing.

Next, signal processing for detecting breathing of the subject Obj using the breathing sensing device 1 will be described using FIG. 6 for cases where the subject Obj performs chest breathing and abdominal breathing as described above. This signal processing is repeatedly executed every prescribed period while the breathing sensing device 1 is driven.

First, in step 1, when the breathing sensing device 1 is driven, the breathing sensing device 1 detects a sensor output generated by the piezoelectric film sensor 3. That is to say, the piezoelectric film sensor 3 deforms due to breathing of the subject Obj (chest breathing and abdominal breathing) and outputs the analog signal Sa to the body part 8. In this case, as illustrated by a characteristic line C1 in FIG. 7, the analog signal Sa generated by the piezoelectric film sensor 3 is a signal that includes both the signal Sk caused by breathing (deformation signal Skh caused by breathing and sound signal Sko caused by breathing) and the signal Ss caused by beating of the heart (deformation signal Ssh caused by beating of the heart and sound signal Sso caused by beating of the heart).

In step 2, the breathing sensing device 1 may perform waveform digital processing on the analog signal Sa output from the piezoelectric film sensor 3. That is to say, the analog signal Sa output from the piezoelectric film sensor 3 may be amplified by the amplifier 9 and converted into the digital signal Sd by the A/D converter 10A of the signal processing unit 10.

In step 3, the signal processing unit 10 of the breathing sensing device 1 may perform frequency filtering and separate the detected analog signal Sa (digital signal Sd) into the deformation signal Skh caused by breathing, the deformation signal Ssh caused by beating of the heart, and the sound signal So. In this case, since the deformation signal Skh caused by breathing, the deformation signal Ssh caused by beating of the heart, and the sound signal So have different frequency components from each other, the signals Skh, Ssh, and So are separated from each other by using different frequency bands when performing the filtering.

Specifically, the frequency component of the deformation signal Skh caused by breathing lies inside the range of 0.05~10 Hz, for example. Furthermore, the frequency component of the deformation signal Ssh caused by beating of the heart lies inside the range 10~50 Hz, for example. In addition, the frequency component of the sound signal So is included in the range of 100~several 1000 Hz, for example.

Therefore, for the case of a component of the digital signal Sd having a frequency f that is lower than a prescribed reference value T1 (f<T1), the processing advances to step 4 and the component is extracted as the deformation signal Skh caused by breathing. In this case, the reference value T1 is set to 10 Hz, for example. In addition, for the case of a component of the digital signal Sd having a frequency f that is greater than or equal to the prescribed reference value T1 and less than or equal to a prescribed reference value T2 (T1<f<T2), the processing advances to step 9 and the component is extracted as the deformation signal Ssh caused by beating of the heart. In this case, the reference value T2 is set to 100 Hz, for example. Furthermore, for the case of a component of the digital signal Sd having a frequency f that is higher than the prescribed reference value T2 (T2<f), the processing advances to step 13 and the component is extracted as the sound signal So.

Figure 10:
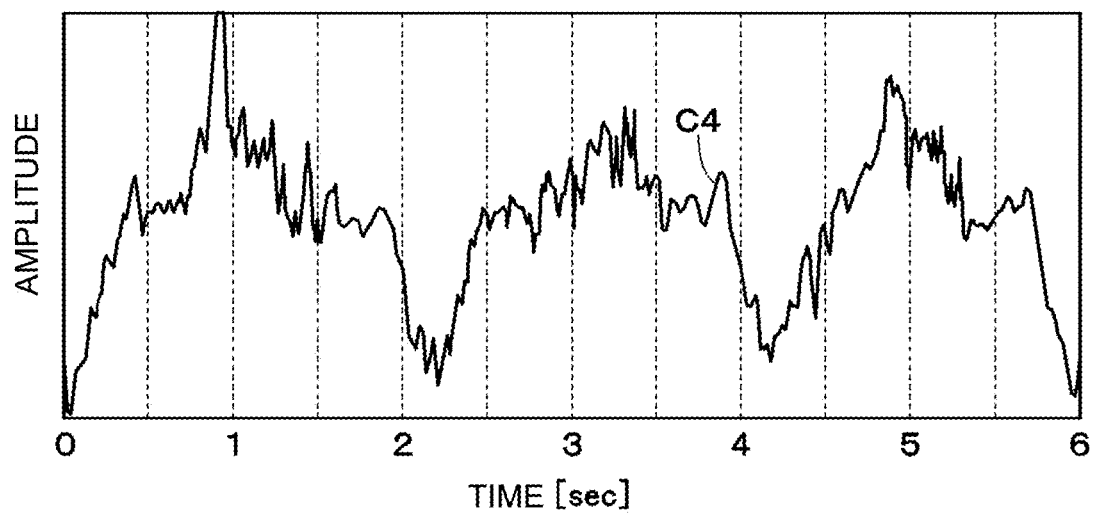
FIG. 10 is a characteristic diagram illustrating changes that occur with respect to time in a deformation signal caused by abdominal breathing.
Figure 11:
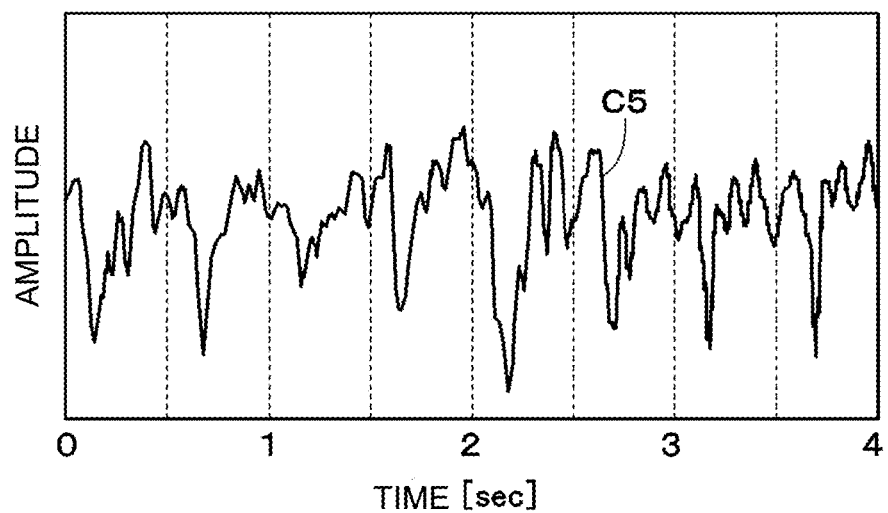
FIG. 11 is a characteristic diagram illustrating changes that occur with respect to time in a deformation signal caused by chest breathing.

Next, in step 4, the signal processing unit 10 extracts the deformation signal Skh caused by breathing. Specifically, the signal processing unit 10 extracts the deformation signal Skh caused by breathing as illustrated by characteristic lines C3 to C5 in FIGS. 9 to 11 on the basis of the signal obtained by the processing performed in step 3 (signal obtained by separating only component having frequency f lower than reference value T1 through filtering). FIG. 10 illustrates an example of measuring abdominal breathing and FIG. 11 illustrates an example of measuring chest breathing. In the measurement example illustrated in FIG. 10, abdominal breathing has a period of approximately 2 seconds. In the measurement example illustrated in FIG. 11, chest breathing has a period of approximately 0.5 seconds. In the measurement examples illustrated in FIGS. 9 to 11, signals caused by beating of the heart have been removed using a frequency filter.

Next, in step 5, the signal processing unit 10 calculates a breathing interval from the deformation signal Skh caused by breathing. Specifically, the signal processing unit 10 may apply a pattern matching method, an autocorrelation technique, or the like to the deformation signal Skh caused by breathing and calculates the breathing interval from a peak interval of a correlation coefficient, though the present disclosure is not limited thereto.

In step 6, the signal processing unit 10 may determine whether the breathing interval calculated in step 5 lies inside a prescribed range. Specifically, the signal processing unit 10 determines whether the breathing interval is between, for example, 0.2-10 seconds. In addition, the signal processing unit 10 also determines whether the correlation coefficient obtained using a pattern matching method or an autocorrelation technique is less than or equal to a prescribed value. In this case, "inside a prescribed range" can be calculated from an average breathing interval calculated in advance using a statistical method or the like.

In the case where the breathing interval does not lie inside the prescribed range or the correlation coefficient is less than or equal to the prescribed value at step 6, an error is produced in step 7. In this case, the signal processing unit 10 may return once again to step 1 and detect the sensor output again, or may instead halt the processing for calculating the breathing interval at that point.

On the other hand, if the breathing interval does lie inside the prescribed range and the correlation coefficient is larger than the prescribed value at step 6, the processing advances to step 8 and the breathing interval is determined. Specifically, the breathing interval calculated in step 5 is decided upon for the breathing of the subject Obj and a breathing rate of the subject Obj inside a prescribed time period is calculated.

Next, in step 9, the signal processing unit 10 may extract the deformation signal Ssh caused by beating of the heart. Specifically, the signal processing unit 10 extracts the deformation signal Ssh caused by beating of the heart as illustrated by characteristic line C2 in FIG. 8 on the basis of a signal obtained by the processing performed in step 3 (signal obtained by separating only component having frequency f between reference value T1 and reference value T2 through filtering).

Next, in step 10, the signal processing unit 10 may calculate the heartbeat interval from the deformation signal Ssh caused by beating of the heart. Specifically, the signal processing unit 10 applies a pattern matching method, an autocorrelation technique, or the like to the deformation signal Shh caused by beating of the heart and calculates the heartbeat interval from a peak interval of a correlation coefficient, though the present disclosure is not limited thereto.

In step 11, the signal processing unit 10 determines whether the heartbeat interval calculated in step 10 is within a particular range, for example, 0.25-1.5 seconds. In addition, the signal processing unit 10 also determines whether the correlation coefficient obtained using a pattern matching method or an autocorrelation technique is less than or equal to a prescribed value. In this case, "inside a prescribed range" can be calculated from an average heartbeat interval calculated in advance using a statistical method or the like.

In the case where the heartbeat interval does not lie inside the prescribed range or the correlation coefficient is less than or equal to the prescribed value in step 11, an error is generated. In this case, the signal processing unit 10 may return once again to step 1 and detect the sensor output again, or may instead halt the processing for calculating the heartbeat interval at that point.

On the other hand, if the heartbeat interval does lie inside the prescribed range and the correlation coefficient is larger than the prescribed value at step 11, the processing advances to step 12 and the heartbeat interval is determined. Specifically, in some aspects the heartbeat interval calculated in step 10 is decided upon as the heartbeat of the subject Obj and a heart rate of the subject Obj inside a prescribed time period is calculated. In this case, when determining the heartbeat interval, the signal processing unit 10 can detect the sound signal So corresponding to the time of the heartbeat interval as the sound signal Sso (heartbeat sound) caused by beating of the heart from the characteristic line C1 illustrated in FIG. 7.

Next, in step 13, the signal processing unit 10 extracts the sound signal So. Specifically, the signal processing unit 10 extracts the sound signal So on the basis of a signal obtained through the processing performed in step 3 (signal obtained by separating only component having frequency f higher than reference value T2 through filtering). In this case, the sound signal So is a signal that includes the sound signal Sko caused by breathing and the sound signal Sso caused by beating of the heart.

Next, in step 14, the signal processing unit 10 removes background noise from the sound signal So. Specifically, the signal processing unit 10 removes background noise, which is small-amplitude high-frequency noise, using an epsilon filter in one example.

In step 15, the signal processing unit 10 removes a heartbeat sound from the sound signal So. Specifically, the signal processing unit 10 removes a heartbeat sound (sound signal Sso caused by beating of heart) detected at the same time as when the heartbeat interval is determined in step 12 from the sound signal So by performing filtering or the like. Thus, the sound signal Sko caused by breathing and the sound signal Sso caused by beating of the heart are separated from the sound signal So.

In step 16, the signal processing unit 10 detects abnormal breathing on the basis of the sound signal Sko caused by breathing, which was separated in step 15. In this case, a normal breathing sound lies in a low sound region (for example, 100 to 1000 Hz), whereas an abnormal breathing sound often lies in a high sound region (1000 to several thousand Hz). Thus, for example, the signal processing unit 10 is able to detect abnormal breathing on the basis of a component ratio between a high sound region and a low sound region and is able to detect abnormal breathing using the wavelet pattern of a high sound region.

In step 17, the signal processing unit 10 extracts an abnormal breathing sound. Specifically, the signal processing unit 10 extracts the sound signal Sko caused by breathing within a prescribed period containing the abnormal breathing detected in step 16.

Next, in step 18, the signal processing unit 10 transmits the breathing interval, the heartbeat interval, and the abnormal breathing sound obtained in steps 8, 12, and 17 to the communication unit 12 that outputs these values to an external device such as a computer, a mobile device, a storage device, a server or the like.

Thus, according to the first embodiment, the piezoelectric film sensor 3 is adhered to a body surface of the subject Obj from a region K corresponding to the xiphoid process of the subject Obj to a region M corresponding to the epigastrium of the subject Obj. Consequently, the piezoelectric film sensor 3 is deformed when the body surface of the subject Obj moves due to breathing and is able detect relative changes between the region K corresponding to the xiphoid process and the region M corresponding to the epigastrium. At this time, a relative displacement is generated between the region K corresponding to the xiphoid process and the region M corresponding to the epigastrium in both chest breathing and abdominal breathing. Therefore, the piezoelectric film sensor 3 can detect both chest breathing and abdominal breathing.

In addition, since the piezoelectric film sensor 3 is only adhered from the region K corresponding to the xiphoid process to the region M corresponding to the epigastrium, the breathing sensing device 1 can be reduced in size compared with a device in which a belt or the like is worn by the subject Obj.

Furthermore, breathing can be detected without compressing the subject Obj with a belt or the like, and therefore a situation in which the breathing of the subject is affected by the device can be suppressed. Thus, a feeling of discomfort experienced by the subject Obj is reduced and the degree of non-invasiveness can be increased.

In addition, the sensor part of the breathing sensing device 1 is constituted by the piezoelectric film sensor 3. Consequently, the displacement speed of a relative change between the region K corresponding to the xiphoid process of the subject Obj and the region M corresponding to the epigastrium of the subject Obj can be measured, and therefore minute body movements of the subject Obj caused by breathing can be accurately detected. In addition, the breathing of the subject Obj can be detected without interference from external disturbances such as perspiration.

Furthermore, the piezoelectric film sensor 3 may have a generally rectangular shape. The breathing sensing device 1 is therefore configured so as to have a high degree of sensitivity to extension in a length direction extending from the chest of the subject Obj to the abdomen of the subject Obj or bending in a front-back direction (thickness direction of piezoelectric film sensor 3) perpendicular to the length direction and so as to have a low degree of sensitivity to twisting. As a result, in the case where the subject Obj changes his/her posture and twisting or the like occurs in the trunk of his/her body, erroneous detection of something other than breathing caused by deformation in the direction of low sensitivity can be suppressed and the piezoelectric film sensor 3 can detect variations due to breathing with high accuracy.

In addition, the breathing sensing device 1 is configured to separate the deformation signal Skh caused by breathing, the sound signal So, and the deformation signal Ssh caused by the beating of the heart as frequency signals having different frequency components from one another by using a frequency filter or the like. As a result, specific signals can be detected by changing the frequency band that is to be detected, and therefore a plurality of signals can be accurately detected using simple processing without the occurrence of erroneous recognition.

In addition, since the deformation signal Skh caused by breathing and the sound signal So are separated and detected, abnormal breathing can be accurately detected by comparing the signals Skh and So. Furthermore, the heartbeat interval (heart rate) can be calculated using the deformation signal Ssh caused by beating of the heart, and therefore a heart abnormality can be detected from the heart rate.

In addition, the breathing sensing device 1 further includes the battery 11 that supplies a power supply voltage to the amplifier 9, the signal processing unit 10, the communication unit 12, and so on, and the signal processing unit 10 is configured to subject a signal output from the sensor member 2 (analog signal Sa) to digital conversion and to output the resulting digital signal to an external device. As a result, breathing can be detected in a cable-free manner, and therefore the non-invasive breathing sensing device 1 can be provided that does not constrict the subject Obj and does not cause the subject Obj to feel stressed or tense. Furthermore, since the device is non-invasive, measurements can also be taken over a long period of time and during everyday activities.

Figure 12:
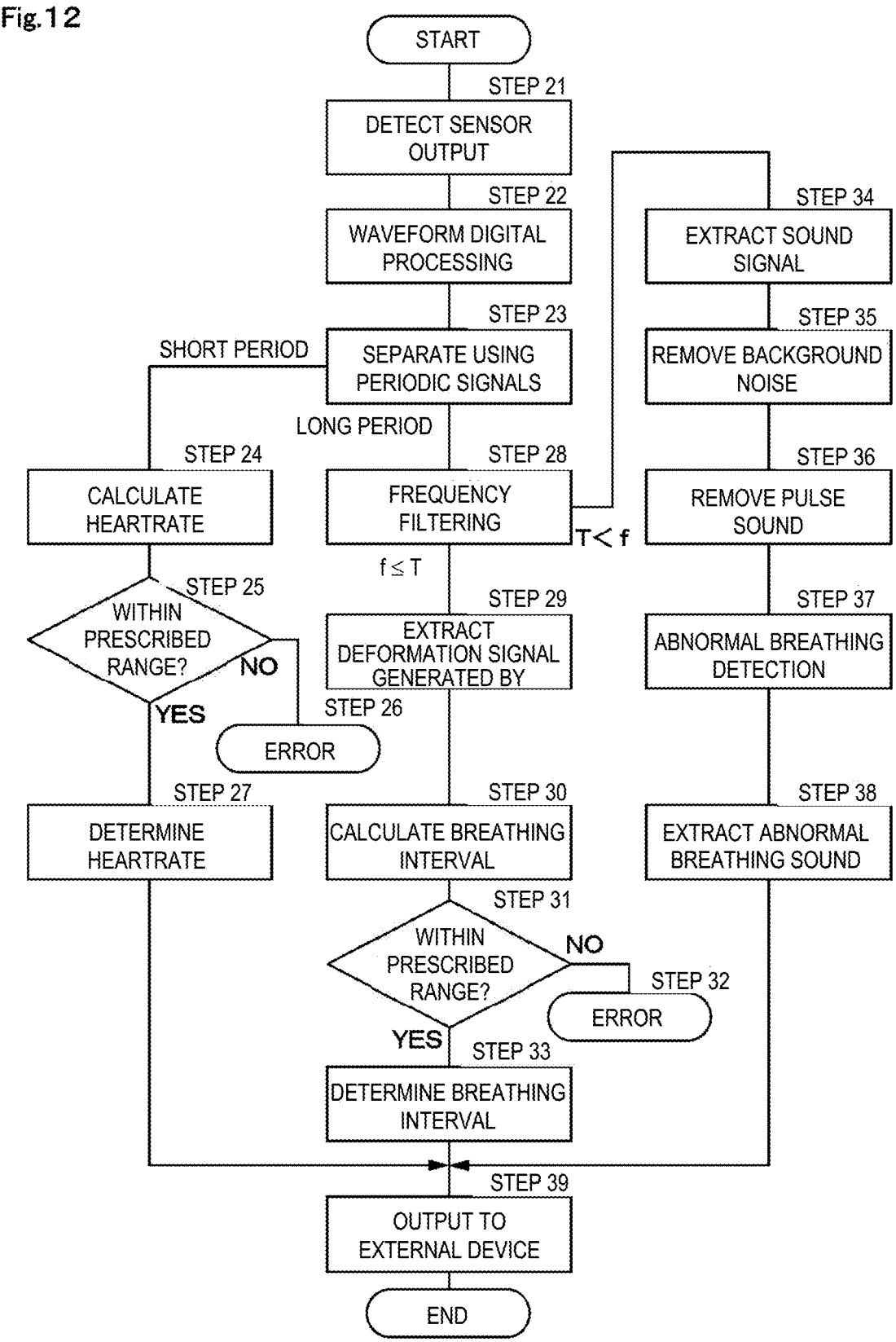
FIG. 12 is a flowchart illustrating breathing sensing processing performed by a breathing sensing device of a second embodiment.

Next, a breathing sensing device according to a second embodiment of the present disclosure is illustrated in FIGS. 1 and 12. A feature of the second embodiment is that the signal Sk caused by breathing and the signal Ss caused by beating of the heart are separated as period signals having different periods from each other. In the second embodiment, constituent elements that are the same as in the first embodiment described above will be denoted by the same symbols and description thereof will be omitted.

Similarly to the first embodiment, a breathing sensing device 21 according to the second embodiment includes a sensor member 2 that detects the breathing of a subject Obj and a body part 8 that performs signal processing on the detected breathing. The body part 8 includes an amplifier 9, a signal processing unit 22, a battery 11, a communication unit 12, and so forth. In this case, the breathing sensing device 21 differs from the breathing sensing device 1 of the first embodiment in that the signal processing unit 22 separates the signal Sk caused by breathing and the signal Ss caused by beating of the heart as period signals having different periods from each other.

The signal processing unit 22 is provided in the body part 8 and has the same configuration as the signal processing unit 10 of the first embodiment. That is to say, the signal processing unit 22 is a signal processing unit that detects the breathing of the subject Obj by processing the analog signal Sa detected by the piezoelectric film sensor 3 in order to separate the analog signal Sa into a signal Sk caused by breathing (deformation signal Skh caused by breathing and sound signal Sko caused by breathing) and a signal Ss caused by beating of the heart (deformation signal Ssh caused by beating of the heart and sound signal Sso caused by beating of the heart).

Subsequently, after converting the analog signal Sa detected by the piezoelectric film sensor 3 into the digital signal Sd, the signal processing unit 22 separates period signals and detects the signal Sk caused by breathing and the signal Ss caused by beating of the heart. In this case, since the signal Sk caused by breathing and the signal Ss caused by beating of the heart have different periods, the signal processing unit 22 is able to separate the signal Sk caused by breathing and the signal Ss caused by beating of the heart as period signals having different periods from each other by using a pattern matching method, an autocorrelation technique, or the like, for example.

The breathing sensing device 21 has the configuration described above, and next, signal processing for detecting breathing of the subject Obj performed by the breathing sensing device 21 for cases where the subject Obj performs chest breathing and abdominal breathing as described above will be described using FIG. 12. This signal processing is repeatedly executed every prescribed period while the breathing sensing device 21 is driven.

First, similarly to step 1 of the first embodiment, in step 21 the breathing sensing device 21 detects a sensor output generated by the piezoelectric film sensor 3.

In step 22, similarly to step 2 in the first embodiment, the breathing sensing device 21 performs waveform digital processing on the analog signal Sa output from the piezoelectric film sensor 3.

In step 23, the signal processing unit 22 of the breathing sensing device 21 separates the detected analog signal Sa (digital signal Sd) into the signal Sk caused by breathing and the signal Ss caused by beating of the heart. In this case, since the signal Sk caused by breathing and the signal Ss caused by beating of the heart have different periods from each other, the signals Sk and Ss are separated by detecting different periods.

Specifically, the period of the signal Sk caused by breathing tends to be relatively long compared with the period of the signal Ss caused by beating of the heart. Consequently, the signal Sk caused by breathing and the signal Ss caused by beating of the heart can be separated by changing the length of the period to be detected. However, since the breathing period may be substantially the same as the beating period of the heart, the signal Sk caused by breathing and the signal Ss caused by beating of the heart are separated not only by using the period range but by also using signal waveform shapes by utilizing a pattern matching method, an autocorrelation technique or the like.

In this case, the breathing sensing device 21 differs from the breathing sensing device 1 of the first embodiment in that the signals Sk and Ss are not separated by filtering frequency components. Therefore, the deformation signal Skh caused by breathing and the sound signal Sko caused by breathing are included in the separated signal Sk caused by breathing and the deformation signal Ssh caused by beating of the heart and the sound signal Sso caused by beating of the heart are included in the separated signal Ss caused by beating of the heart.

Therefore, for the signal Ss caused by beating of the heart extracted from the digital signal Sd, the processing advances to step 24 and the heartbeat interval is calculated. In this case, the beating period of the heart is set to be 0.25-1.5 seconds, for example. Furthermore, for the signal Sk caused by breathing extracted from the digital signal Sd, the processing advances to step 28 and frequency filtering is performed. In this case, the breathing period is set to 0.2-10 seconds, for example. Other varying periods are also contemplated herein.

Next, in step 24, similarly to step 10 in the first embodiment, the signal processing unit 22 calculates the heartbeat interval from the signal Ss caused by beating of the heart.

In step 25, similarly to step 11 in the first embodiment, the signal processing unit 22 determines whether the heartbeat interval calculated in step 24 lies inside a prescribed range. In addition, the signal processing unit 22 also determines whether the correlation coefficient obtained using a pattern matching method or an autocorrelation technique is less than or equal to a prescribed value.

In the case where the heartbeat interval does not lie inside the prescribed range or the correlation coefficient is less than or equal to the prescribed value at step 25, an error is generated in step 26.

On the other hand, if the heartbeat interval does lie inside the prescribed range and the correlation coefficient is larger than the prescribed value in step 25, the processing advances to step 27 and the heartbeat interval is determined. Specifically, the heartbeat interval calculated in step 24 is decided upon as the heartbeat of the subject Obj and the signal processing unit 22 calculates the heart rate of the subject Obj inside a prescribed time period. In this case, when determining the heartbeat interval, the signal processing unit 22 can detect the sound signal So corresponding to the time of the heartbeat interval as the sound signal Sso (heartbeat sound) caused by beating of the heart.

Next, in step 28, the signal processing unit 22 performs frequency filtering, and separates the signal Sk caused by breathing separated in step 23 into the deformation signal Skh caused by breathing and the sound signal So. In this case, since the deformation signal Skh caused by breathing and the sound signal So have different frequency components from each other, the signals Skh and So are separated by using different frequency bands when performing the filtering.

Therefore, for the case of a component of the signal Sk caused by breathing having a frequency f that is less than or equal to a prescribed reference value T (f<T), the processing advances to step 29 and the component is extracted as the deformation signal Skh caused by breathing. In this case, the reference value T is set to 10 Hz, for example. Furthermore, for the case of a component of the signal Sk caused by breathing having a frequency f that is higher than the prescribed reference value T (T<f), the processing advances to step 34 and the component is extracted as the sound signal So.

Next, in step 29, similarly to step 4 in the first embodiment, the signal processing unit 22 extracts the deformation signal Skh caused by breathing.

Next, in step 30, similarly to step 5 in the first embodiment, the signal processing unit 22 calculates the breathing interval from the deformation signal Skh caused by breathing.

In step 31, similarly to step 6 in the first embodiment, the signal processing unit 22 determines whether the breathing interval calculated in step 30 lies inside a prescribed range. In addition, the signal processing unit 22 also determines whether the correlation coefficient obtained using a pattern matching method or an autocorrelation technique is less than or equal to a prescribed value.

In the case where the breathing interval does not lie inside the prescribed range or the correlation coefficient is less than or equal to the prescribed value at step 31, the signal processing unit 22 produces an error in step 32.

On the other hand, if the breathing interval does lie inside the prescribed range and the correlation coefficient is larger than the prescribed value in step 31, the processing advances to step 33 and the signal processing unit 22 determines the breathing interval.

Next, in step 34, similarly to step 13 in the first embodiment, the signal processing unit 22 extracts the sound signal So.

Next, in step 35, similarly to step 14 in the first embodiment, the signal processing unit 22 removes background noise from the sound signal So.

In step 36, similarly to step 15 in the first embodiment, the signal processing unit 22 removes the heartbeat sound (sound signal Sso caused by beating of heart) from the sound signal So.

In step 37, similarly to step 16 in the first embodiment, the signal processing unit 22 detects abnormal breathing on the basis of the sound signal Sko caused by breathing.

In step 38, similarly to step 17 in the first embodiment, the signal processing unit 22 extracts an abnormal breathing sound.

Next, in step 39, similarly to step 18 in the first embodiment, the signal processing unit 22 transmits the breathing interval, the heartbeat interval, and the abnormal breathing sound obtained in steps 27, 33, and 38 to the communication unit 12, and the communication unit 12 outputs these signals to an external device (e.g., any computing device storage server or the like).

Thus, substantially the same operational effect can be obtained in the second embodiment as in the first embodiment. According to the second embodiment, the breathing sensing device 21 is configured to separate the signal Sk caused by breathing and the signal Ss caused by beating of the heart as period signals having different periods from each other using a pattern matching method, an autocorrelation technique, or the like. Thus, even in the case where frequency components of the individual signals overlap and cannot be separated from each other using a frequency filter, specific signals can be detected by changing the period to be detected. Therefore, a plurality of signals can be accurately detected without the occurrence of erroneous recognition.

In addition, the breathing rate of the subject Obj can be accurately detected by estimating breathing fluctuations (fluctuations of body surface of subject Obj caused by breathing) of the subject Obj from the signal Ss caused by beating of the heart and comparing the breathing fluctuations and the signal Sk caused by breathing.

Figure 13:
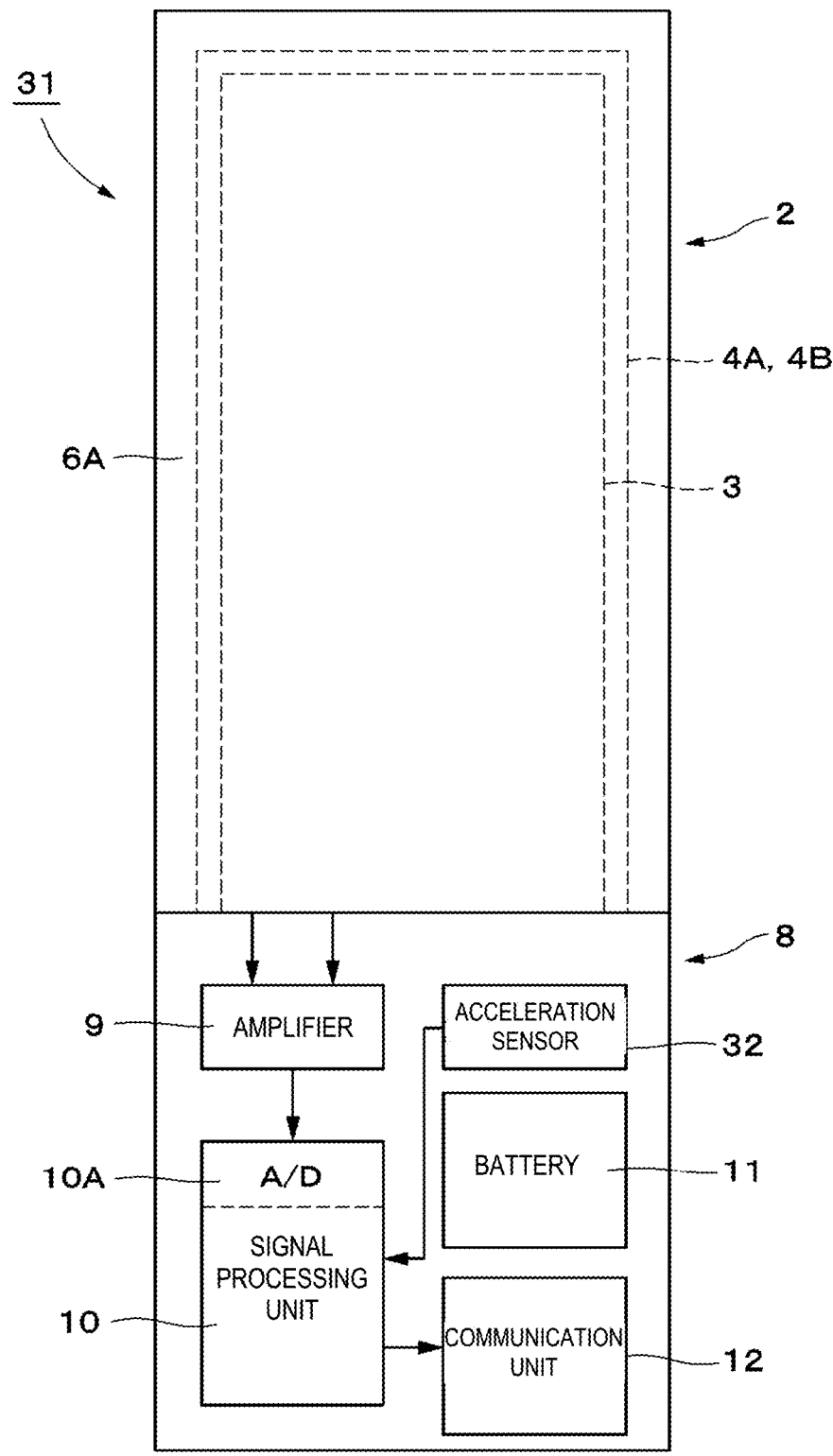
FIG. 13 is a front view illustrating a breathing sensing device according to a third embodiment.

Next, a breathing sensing device according to a third embodiment of the present disclosure is illustrated in FIG. 13. A feature of the third embodiment is that the breathing sensing device includes an acceleration sensor. In the third embodiment, constituent elements that are the same as in the first embodiment described above will be denoted by the same symbols and description thereof will be omitted.

Similarly to the first embodiment, a breathing sensing device 31 according to the third embodiment includes a sensor member 2 that detects the breathing of a subject Obj and a body part 8 that performs signal processing on the detected breathing. The body part 8 includes an amplifier 9, a signal processing unit 10, a battery 11, a communication unit 12, an acceleration sensor 32, and so forth. In this case, the breathing sensing device 31 differs from the breathing sensing device 1 of the first embodiment in that the breathing sensing device 31 includes the acceleration sensor 32.

The acceleration sensor 32 is provided in the body part 8 and is connected to the signal processing unit 10. The acceleration sensor 32 includes an A/D converter (not illustrated) for example, and operates through power supplied from the battery 11. In some aspects, the A/D converter is built into the accelerometer. The acceleration sensor 32 detects the posture and activity amount of the subject Obj as an acceleration signal and outputs the acceleration signal to the signal processing unit 10. In this case, the posture of the subject Obj refers to a posture when the subject Obj is standing, when the subject Obj is in a state of sleeping (lying down), and so on. In addition, for example, the activity amount of the subject Obj refers to an activity amount when the subject Obj is resting, when the subject is exercising, and so on.

Thus, substantially the same operational effect can be obtained in the third embodiment as in the first embodiment. According to the third embodiment, the breathing sensing device 31 includes the acceleration sensor 32. Thus, information regarding the posture and activity amount of the subject Obj, which are factors that affect breathing and beating of the heart can be simultaneously obtained, and therefore an abnormality in the breathing or the beating of the heart can be accurately detected. For example, breathing slowly becomes deeper during deep sleep and beating of the heart also becomes slower. In contrast, breathing and beating of the heart both become faster while walking or during exercise. Therefore, the accuracy with which an abnormality is detected can be improved by simultaneously obtaining information regarding posture and activity amount.

In the first embodiment, the breathing sensing device 1 is configured to convert the analog signal Sa into the digital signal Sd using the A/D converter 10A and then perform frequency filtering on the digital signal Sd. However, the present disclosure is not limited to this configuration, and the analog signal Sa may be subjected to frequency filtering using an analog filter. This also applies to the second and third embodiments.

Furthermore, the first embodiment has a configuration in which signal processing is performed using the signal processing unit 10 provided in the body part 8. However, the present disclosure is not limited to this configuration and a configuration may instead be adopted in which the signal processing is performed in an external device. This also applies to the second and third embodiments.

In addition, the first embodiment has a configuration in which the communication unit 12 is provided in the body part 8 and the breathing interval, the heartbeat interval, and the abnormal breathing sound are output in real-time to an external device using the communication unit 12. However, the present disclosure is not limited to this configuration, and a configuration may instead be adopted in which the breathing sensing device and an external device are connected to each other using a cable and various types of data are output using wired communication. In this case, a configuration may be adopted in which various types of data are temporarily stored in a memory (not illustrated) provided in the body part and are output to an external device once all the measurements are completed. In addition, power may be supplied using a cable. This also applies to the second and third embodiments.

Furthermore, in the first and second embodiments, the breathing sensing devices 1 and 21 include the film sensor 3 as a sensor, and in the third embodiment, the breathing sensing device 31 includes the film sensor 3 and the acceleration sensor 32 as sensors. However, the present disclosure is not limited to these configurations, and for example, sensors such as an electrocardiogram sensor, a pulse wave sensor, a temperature sensor, and so forth may be used in combination with each other. It is easy to separate a deformation signal caused by beating of the heart and a sound signal by simultaneously obtaining information regarding the beating of the heart using an electrocardiogram sensor, a pulse wave sensor, and so on, and the accuracy with which a movement state and a sleeping state, which affect the breathing, can be improved by using a temperature sensor or the like in combination with an acceleration sensor. Furthermore, it is possible to detect a fever resulting from an ailment or the like from a raised temperature and abnormal breathing.

Furthermore, in the first embodiment, the piezoelectric film sensor 3 is used as a sensor. However, the present disclosure is not limited to this configuration and an electrostatic capacitance sensor, a strain gauge, a microphone and so forth may be used as sensors. This also applies to the second and third embodiments.

REFERENCE SIGNS LIST

1, 21, 31 breathing sensing device
3 piezoelectric film sensor
10, 22 signal processing unit
11 battery
32 acceleration sensor

What is claimed is:
1. A breathing sensing device that detects breathing of a subject, the breathing sensing device comprising:
 a film-shaped sensor configured to adhere to a body surface of the subject, wherein the size of the film-shaped sensor corresponds to dimensions extending from a region corresponding to a xiphoid process of a sternum of the subject to a region corresponding to an epigastrium of the subject,
 wherein the film-shaped sensor is configured to be adhered only to the region corresponding to the xiphoid process and the region corresponding to the epigastrium,
 and wherein the film-shaped sensor is configured to detect the breathing of the subject based on relative positional changes caused by movement of the region corresponding to the xiphoid process and movement of the region corresponding to the epigastrium;
 a signal processing unit configured to:
  extract, from an output of the film-shaped sensor, a breathing deformation signal from frequency components of the output that are below a first reference value and a sound signal from frequency components of the output that are greater than a second reference value; and
  detect abnormal breathing by comparing the breathing deformation signal and the sound signal.

2. The breathing sensing device according to claim 1, wherein the film-shaped sensor is a piezoelectric film sensor and is configured to detect the breathing of the subject by detecting a signal generated by deformation of the piezoelectric film sensor.

3. The breathing sensing device according to claim 1, wherein the film-shaped sensor has a rectangular shape, has a degree of sensitivity greater than a threshold value to extension in a length direction extending from a chest of the subject to an abdomen of the subject or bending in a front-back direction perpendicular to the length direction and has a degree less than a threshold value of sensitivity to twisting.

4. The breathing sensing device according to claim 1, wherein the film-shaped sensor is further configured to:
 measure a displacement speed of the relative change in the region; and
 detect minute body movements of the subject based on the displacement speed.

5. The breathing sensing device according to claim 1, further comprising:
 a signal processing unit configured to separate the output from the film-shaped sensor caused by breathing of the subject, the sound signal, and by beating of a heart based on filtering the output using the frequency components of the output.

6. The breathing sensing device of claim 5, wherein the signal processing unit is further configured to:
 extract a heartbeat deformation signal from the frequency components of the output that are between the first reference value and a second reference value.

7. The breathing sensing device according to claim 6, wherein the signal processing unit is further configured to:
 calculate a breathing interval of the breathing deformation signal;
 determine whether the breathing interval is within a predetermined breathing range; and
 in response to determining whether the breathing interval is within the predetermined breathing range, determining a breathing rate within a period of time of the subject.

8. The breathing sensing device according to claim 7, wherein the signal processing unit is further configured to:
 calculate a heartbeat interval of the heartbeat deformation signal;
 determine whether the heartbeat interval is within a predetermined heartbeat range; and
 in response to determining whether the heartbeat interval is within the predetermined heartbeat range, determining a heart rate for a period of time of the subject.

9. The breathing sensing device according to claim 7, wherein the signal processing unit is further configured to:
 remove background noise of the sound signal;
 remove pulse sound of the sound signal; and
 detect whether the sound signal indicates abnormal breathing; and
 in response to detecting abnormal breathing, extracting a sound associated with the abnormal breathing of the subject.

10. The breathing sensing device of claim 9, wherein the signal processing unit is configured to calculate the breathing interval and/or a heartbeat interval using one of pattern matching or an autocorrelation technique, and
 wherein the signal processing unit is configured to remove the background noise using an epsilon filter.

11. The breathing sensing device of claim 9, wherein the signal processing unit is configured to detect that the sound signal indicates abnormal breathing when a wavelet pattern of the sound signal is in a high sound region.

12. The breathing sensing device of claim 6, further comprising:
determining a period of a signal; and
determining, based on the period of the signal, whether the signal is caused by breathing or is caused by beating of the heart.

13. The breathing sensing device according to claim 5, further comprising:
a battery configured to supply a power supply voltage to the signal processing unit,
wherein the signal processing unit is configured to convert a signal output from the film-shaped sensor into a digital signal and output the digital signal to an external device.

14. The breathing sensing device according to claim 1, further comprising:
an acceleration sensor configured to detect an acceleration signal and to determine a posture and an activity amount of the subject based on the acceleration signal.

15. The breathing sensing device according to claim 14, wherein the acceleration sensor is configured to:
determine whether the subject is in a state of sleeping, walking or exercising based on the posture and the activity amount; and
identify abnormal breathing based on the state of the subject.

16. The breathing sensing device according to claim 14, further comprising:
an electrocardiogram sensor configured to separate a deformation signal caused by a heartbeat of the subject and a simultaneous sound signal detected by the film-shaped sensor.

17. The breathing sensing device according to claim 14, further comprising:
a temperature sensor configured to improve accuracy of the posture and the activity amount calculated by the acceleration sensor.

18. The breathing sensing device according to claim 17, further comprising:
a signal processing unit configured to detect a fever of the subject based on output from the acceleration sensor and the temperature sensor.

19. A breathing sensing device that detects breathing of a subject, the breathing sensing device comprising:
a substantially rectangular sensor member comprising:
a film sensor configured to generate an electrical signal when deformed;
one or more electrodes located on both sides of the film sensor, configured to detect the electrical signal corresponding to the deformation;
one or more shields located outside of the sensor member, configured to shield the film sensor from external signals;
one or more insulating sheets located on both sides of the film sensor and the one or more electrodes, configured to insulate the one or more electrodes from the one or more shields; and
wherein the size of the substantially rectangular sensor member corresponds to dimensions extending from a region corresponding to a xiphoid process of a sternum of the subject to a region M corresponding to an epigastrium of the subject;
an adhesive member located on one side of the breathing sensing device, and configured to adhere to a body of a subject in the region corresponding to the xiphoid process of the sternum of a subject to the region M corresponding to the epigastrium of the subject, wherein the breathing sensing device is configured to detect the breathing of the subject by determining relative positional changes caused by movements detected between only the region corresponding to the xiphoid process and the region M corresponding to the epigastrium; and
a body part member located at a distal end of the breathing sensing device, comprising:
an amplifier configured to amplify the signal generated by the one or more electrodes;
a signal processing unit configured to:
receive the amplified signals and detect the breathing of the subject;
extract, from an output of the film sensor, a breathing deformation signal from frequency components of the output that are below a first reference value and a sound signal from frequency components of the output that are greater than a second reference value; and
detect abnormal breathing by comparing the breathing deformation signal and the sound signal;
a battery configured to supply power to components of the body part member; and
a communication unit configured to receive information regarding the breathing of the subject, and output information about the subject to a computing device.

* * * * *